United States Patent

Wätjen

[11] Patent Number: 4,845,095
[45] Date of Patent: Jul. 4, 1989

[54] 4-PHENYLPIPERIDINE COMPOUNDS AND THEIR USE

[75] Inventor: Frank Wätjen, Ravnehusvej, Denmark

[73] Assignee: A/S Ferrosan, Soeborg, Denmark

[21] Appl. No.: 172,197

[22] Filed: Mar. 23, 1988

[30] Foreign Application Priority Data

Mar. 31, 1987 [DK] Denmark .................. 1620/87

[51] Int. Cl.$^4$ .................. A61K 31/445; A61K 31/41; C07D 413/04; C07D 211/28
[52] U.S. Cl. .................. 514/326; 546/209; 546/239; 514/331
[58] Field of Search .............. 514/232, 331; 546/209, 546/239

[56] References Cited

U.S. PATENT DOCUMENTS 4,016,170  4/1977  Nadelson .................. 546/209

Primary Examiner—Robert T. Bond
Attorney, Agent, or Firm—Gordon W. Hueschen

[57] ABSTRACT

Piperidine compounds having the formula

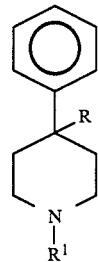

wherein
$R^1$ is hydrogen, ($C_{1-6}$-alkoxyaryl)alkyl, diphenylmethozy-$C_{1-6}$-alkyl, $C_{1-8}$-alkyl, $C_{4-10}$-cycloalkylalkyl, phenoxy-$C_{1-8}$-alkyl, or $C_{1-6}$-alkoxy-$C_{1-6}$-alkyl; and
R is

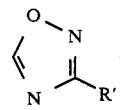

or CH=NOR' wherein
R' is $C_{1-6}$-alkyl, $C_{3-7}$-cycloalkyl, $C_{1-6}$-alkoxy-$C_{1-6}$-alkyl, aryl-$C_{0-6}$-alkyl, which may optionally be substituted with one or more halogen and ($_{1-5}$-alkoxy, thienyl, or $C_{4-7}$-cycloalkylalkyl.

The novel compounds are useful for the treatment of pain conditions and as neuroleptics.

8 Claims, No Drawings

4-PHENYLPIPERIDINE COMPOUNDS AND THEIR USE

The present invention relates to therapeutically active piperidine compounds, a method of preparing the same, and to pharmaceutical compositions comprising the compounds. The novel compounds are useful for treating pain conditions. Pethidine is well known for its potent pain relieving activity, and is a widely used drug for treating surgery assosiated pain conditions, acute pain conditions, such as gallstone-and renal colic, and for pain relief for desolate cancer cases. Pethidine however also possesses a high addiction potential, as well as causing a series of highly frequent side effects. It is therefore of interest to find new compounds having the pain relieving potential of pethidine. It has now been found, that members of a novel group of piperidine compounds analouges have a strong pain relieving activity and further have neuroleptic activity. Accordingly it is an object of the invention to provide such novel piperidine compounds. The 4-phenylpiperidine compounds of the invention have the general formula I

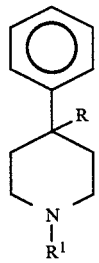

(I)

wherein
$R^1$ is hydrogen, ($C_{1-6}$-alkoxyaryl)alkyl, diphenylmethoxy-$C_{1-6}$-alkyl, $C_{1-8}$-alkyl, $C_{4-10}$-cycloalkylalkyl, phenoxy- $C_{1-8}$-alkyl, or $C_{1-6}$-alkoxy-$C_{1-6}$alkyl; and
R is

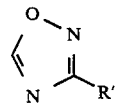

or CH=NOR' wherein
R' is $C_{1-6}$-alkyl, $C_{3-7}$-cycloalkyl, $C_{1-6}$-alkoxy-$C_{1-6}$-alkyl, aryl-$C_{0-6}$-alkyl, which may optionally be substituted with one or more halogen and $C_{1-5}$-alkoxy, thienyl, or $C_{4-7}$-cycloalkylalkyl.

The invention also relates to a method of preparing the above mentioned compounds. This methods comprises:

(a) reacting a reactive derivative of a compound having the general formula II

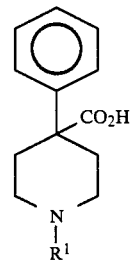

(II)

wherein $R^1$ has the meaning set forth above, with a compound having the general formula III

 R'—C(=NOH)NH₂   (III)

wherein R' has the meaning set forth above, to form a compound of the general formula I, or (b) reacting a compound having the general formula IV

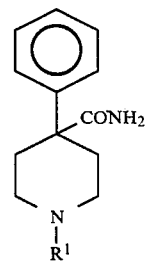

(IV)

wherein $R^1$ has the meaning set forth above, with a compound having the general formula V

R'—C(OCH₃)₂N(CH₃)₂   (V)

wherein R' has the meaning set forth above, to form a compound having the general formula VI

(VI)

wherein $R^1$ and R' have the meanings set forth above, and reacting the compound having the formula VI with hydroxylamine or another aminating agent, to form a compound having the general formula I, or (c) reacting a compound having the general formula VII

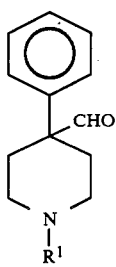

wherein R¹ has the meaning set forth above with a compound having the formula NH₂—O—R′, wherein R′ has the meaning set forth above, to form a compound having the general formula I, or (d) reacting a compound having the general formula VIII

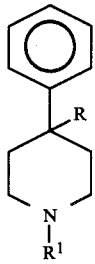

wherein R and R¹ have the meanings set forth above, provided however that R¹ is not hydrogen, with a dealkylating agent, to form a compound having the general formula I wherein R¹ is hydrogen, or (e) reacting a compound having the general formula IX

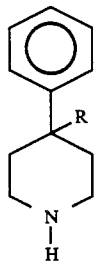

wherein R has the meaning set forth above, with an alkylating agent, to form a compound having the general formula I.

The pharmaceutical properties of the compounds of the invention can be illustrated by determining their capability to antagonize the acetic acid induced writhing syndrome in mice.

Principle:

In mice i.p. injection of acetic acid induces a writhing syndrome which is antagonized by analgesics (Siegmund et al., Proc. Soc. exp. Biol. 95, 729–731 (1957); Eckhardt et al., Proc. Soc. exp. Biol. 98, 186–188 (1958).

Test procedure: Acetic acid 0.5 per cent is injected i.p. (0.15 ml/10g body weight) to 6 mice (NMRI, either sex weighing 20–25 g) pretreated with physiological saline (controls) and to 6 mice pretreated with test substance. In the controls acetic acid induces a syndrome characterized by contraction of abdomen, turning of trunk and extension of hind limbs. Saline and test substances are administered s.c. 30 minutes before acetic acid. The number of writhings is counted 5–15 minutes after injection of acetic acid. The activity is expressed as per cent protection=

(Control drug)/Control × 100

The effect of active substances is evaluated by a dose response curve, log dose on the abscissa, and per cent protection on the ordinate. The potency is expressed as the dose (ED₅₀) in mg/kg giving 50 per cent protection against writhings. Test results obtained by testing some compounds of the invention will appear from the following table.

TABLE

|  | ED₅₀ mg/kg |
| --- | --- |
| Compound 1 | 5.7 |
| Compound 2 | 7.6 |
| Compound 3 | (41% inhibition at 3 partial agonists) |
| Compound 4 | 3.0 |
| Compound 10 | 3.2 |
| Compound 13 | 2.9 |
| Compound 16 | (34% inhibition at 10 partial agonists) |
| Pethidine | 9.25 |

The compounds of the invention, together with a conventional adjuvant, carrier, or diluent, and if desired in the form of a pharmaceutically-acceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective pain relieving amount of the active ingredient commensurate with the intended daily dosage range to be employed. Tablets containing ten (10) milligrams of active ingredient or, more broadly, one (1) to hundred (100) milligrams, per tablet, are accordingly suitable representative unit dosage forms.

The compounds of this invention can thus be used for the formulation of pharmaceutical preparations, e.g., for oral and parenteral administration to mammals including humans, in accordance with conventional methods of galenic pharmacy.

Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Ampoules are convenient unit dosage forms.

Tablets, dragees, or capsules having talc and/or a carbohydrate carrier or binder or the like, the carrier preferably being lactose and/or corn starch and/or potato starch, are particularly suitable for oral application. A syrup, elixir or the like can be used in cases where a sweetened vehicle can be empolyed.

Generally, the compounds of this invention are dispensed in unit form comprising 1–100 mg in a pharmaceutically acceptable carrier per unit dosage.

The dosage of the compounds according to this invention is 1–100 mg/day, preferably 10–30 mg/day, when administered to patients, e.g. humans, as a drug.

A typical tablet which may be prepared by conventional tabletting techniques contains:
Active compound: 10.0 mg
Lactosum: 67.8 mg Ph.Eur.
Avicel ®: 31.4 mg
Amberlite ®IRP 88: 1.0 mg
Magnesii stearas: 0.25 mg Ph.Eur.

Due to the high pain relieving activity, the compounds of the invention are extremely useful in the treatment of pain conditions, when administered in an amount effective for relieving such pain conditions. The important pain relieving activity of the compounds of the invention includes high activity in the treatment of pain conditions associated with surgery, acute pain, such as gallstone- and renal colic, and cancer associated pain. The compounds of the invention may accordingly be administered to a subject, e.g., a living animal body, including a human, in need of pain relief, and if desired in the form of a pharmaceutically-acceptable acid addition salt thereof (such as the hydrobromide, hydrochloride, or sulfate, in any event prepared in the usual or conventional manner, e.g., evaporation to dryness of the free base in solution together with the acid), ordinarily concurrently, simultaneously, or together with a pharmaceuticallyacceptable carrier or diluent, especially and preferably in the form of a pharmaceutical composition thereof, whether by oral, rectal, or parenteral (including subcutaneous) route, in an effective pain relieving amount, and in any event an amount which is effective for relieving pain conditions. Suitable dosage ranges are 1–100 milligrams daily, especially 10–30 milligrams daily, depending as usual upon the exact mode of administration, form in which administered, the indication toward which the administration is directed, the subject involved and the body weight of the subject involved, and the preference and experience of the physician or veterinarian in charge.

The invention will now be described in further detail with reference to the following examples:

EXAMPLE 1 a. Methoxyacetamide oxime 2,3 g of sodium in 33 ml of dry methanol was mixed with 6,55 g of hydroxylamine hydrochloride in 66 ml of dry methanol. The mixture was filtered and 7,8 g of methoxyacetonitrile was added dropwise to the filtrate. The mixture was left for 48 h. The mixture was then cooled to 4° C. Filtration and evaporation of the filtrate give 8,7 g of the title compound.

The following compounds were synthesized from the appropriate nitriles in an analogous manner:
2-thienylcarboxamidoxime
benzamide oxime
acetamide oxime
propionamide oxime
isopropyl carboxamide oxime
cyclopropyl carboxamide oxime
2-(2-methoxyphenyl)-acetamide oxime
1-naphtylcarboxamide oxime
2-chloro-6-fluorobenzamide oxime
2-fluorobenzamid oxime b. 1-Mthyl-4-phenylpiperidine-4-carboxylic acid imidazolide

To a stirred suspension of 1-methyl-4-phenylpiperidine-4-carboxylic acid (1,9 g, 8,7 mmol) in refluxing tetrahydrofuran (THF) was added carbonyldiimidazole (3,0 g, 18 mmol). After 30 min. reflux a clear solution was observed containing the title compound.

c. 1-Methyl-4-(3-methyl-1,2,4-oxadiazol-5-yl)-4-phenylpiperidine hydrochloride (Compound 1)

To the aforementioned solution was added at room temperature acetamideoxime (1,5 g, 20 mmol) whereafter the reaction mixture was heated with stirring to reflux temperature for 1½ h. THF was evaporated in vacuo, whereafter the residue was treated with refluxing toluene (30 ml) for 9 h. The solvent was evaporated in vacuo and the oily residue was partitioned between diethylether/water. The organic phase was then dried over Na₂SO₄ and evaporated to give the title compound as its free base. The hydrochloride was precipitated from an isopropanolic solution with HCl in diethylether, M.p. 260°–263° C.

The following compounds were prepared in an analogous manner from the appropriate amide oximes:
1-methyl-4-(3-cyclopropyl-1,2,4-oxadiazol-5-yl)-4-phenylpiperidine hydrochloride, M.p. 228°–232° C. (Compound 2)
1-methyl-4-(3-phenyl-1,2,4-oxadiazol-5-yl)-4-phenylpiperidine, M.p. 102.9°–103.1° C. (Compound 3)
1-methyl-4-(3-methoxymethyl-1,2,4-oxadiazol-5-yl)-4-phenylpiperidine hydrochloride, M.p. 189°–191° C. (Compound 4)
1-methyl-4-(3-(2-thienyl)-1,2,4-oxadiazol-5-yl)-4-phenylpiperidine oxalate, M.p. 209°–210° C. (Compound 5)
1-methyl-4-(3-(2-methoxyphenyl)methyl-1,2,4-oxadiazol-5-yl) 4-phenylpiperidine oxalate, M.p. 181°–183° C. (Compound 6)
1-methyl-4-(3-(1-naphtyl)-1,2,4-oxadiazol-5-yl)-4-phenylpiperidine oxalate, M.p. 184–°185° C. (Compound 7)
1-methyl-4-(3-(2-chloro-6-fluorophenyl)-1,2,4-oxadiazol-5-yl) 4-phenylpiperidine oxalate, M.p. 177°–178° C. (Compound 8)
1-methyl-(3-(2-fluorophenyl)-1,2,4-oxadiazol-5-yl)-4-phenylpiperidine oxalate, M.p. 183°–184° C. (Compound 9)

EXAMPLE 2 a. 1-Methyl-4-phenylpiperidine-4-carboxaldehyde

Ethyl 1-methyl-4-phenylpiperidine-4-carboxylate (2.7 g, 10 mmol) was dissolved in dry toluene (30 ml). The stirred solution was cooled to −63° C. under an atmosphere of $N_2$, whereafter a solution of diisobutylaluminiumhydrid (DIBAH, 1 M, 20 ml) was added dropwise. Stirring was continued at $-70°$ C. for 1½ h, whereafter methanol (5 ml) was added, in order to destroy excess of DIBAH. At ambient temperature water (50 ml) was added, and the mixture was filtered through a pad of filter aid. The organic phase was dried over $Na_2SO_4$ and evaporated to leave an oily residue. Treatment with ether afforded precipitation of the side product 4-hydroxymethyl-1-methyl-4-phenylpiperidine as pale crystals. Filtration followed by evaporation of the filtrate left the title compound as an oil, which was processed without further purification.

b.

4-Methoxyiminomethyl-1-methyl-4-phenyl-piperidine oxalate (Compound 10)

A mixture of 1-methyl-4-phenylpiperidine-4-carboxaldehyde (0,2 g, 1 mmol), O-methylhydroxylamine hydrochloride (0,15 g, 1,8 mmol) and triethylamine (0,5 ml) was dissolved in methanol. The solution was left at room temperature for 24 h, and then evaporated to give an oily residue, which was partitioned between methylene chloride (50 ml) and water (50 ml). The organic phase was dried over $Na_2SO_4$ and evaporated. The residue was then redissolved in diethylether (20 ml) and charged with an ethanolic solution of oxalic acid, whereby the title compound precipitated as white crystals. The crystals were collected by filtration and washed with diethylether, M.p. 149°–150° C.

In a similar manner was prepared:
4-cyclopropylmethoxyiminomethyl-1-methyl-4-phenylpiperidine from 0-cyclopropylmethylhydroxylamine hydrochloride, isolated as an oil. (Compound 11)

EXAMPLE 3

4-(3-Methyl-1,2,4-oxadiazol-5-yl)-4-phenylpiperidine (Compound 12)

To a solution of 1-methyl-4-(3-methyl-1,2,4-oxadiazol-5-yl)-4-phenylpiperidine (2,1 g, 8,2 mmol) in dry toluene (50 ml) was added 1-chloroethyl chloroformate (1,3 ml, 12 mmol). After stirring for 10 min. at room temperature the solution was heated to 80° C. for 2½h, then cooled to 0° C. where unreacted starting material was filtered off as its hydrochloride. After evaporation of the filtrate the residue was dissolved in methanol (40 ml) and heated to reflux temperature for 3 h whereafter the solvent was evaporated in vacuo. The residue was then partitioned between diethylether (50 ml) and water (100 ml). The aqueous phase was separated and pH was adjusted to 9 with $K_2CO_3$ whereby the title compound precipitated as an oil, which crystallized upon standing, M.p. 114–°117° C.

In a similar manner the following compounds were prepared starting from their 1-methyl derivatives:
4-(3-cyclopropyl-1,2,4-oxadiazol-5-yl)-4-phenylpiperidine, M.p. 108°–109° C. (Compound 13).
4-(3-phenyl-1,2,4-oxadiazol-5-yl)-4-phenylpiperidine hydrochloride, M.p. 111,3°–111,6° C. (Compound 14)
4-(3-(-1-naphtyl)-1,2,4-oxadiazol-5-yl)-4-phenylpiperidine oxalate, M.p. 185°–186° C. (Compound 15)

EXAMPLE 4

4-(3-cyclopropyl-1,2,4-oxadiazol-5-yl)-1-(4-phenoxybutyl)-4-phenylpiperidine oxalate (Compound 16)

A mixture of 4-(3-cyclopropyl-1,2,4-oxadiazol-5-yl)-4-phenylpiperidine (0,54 g, 2 mmol), $K_2CO_3$ (0,5 g, 4,3 mmol) and 4-phenoxybutylbromide (0,66 g, 2,9 mmol) was heated with stirring to reflux temperature in 99,9% ethanol (25 ml) for 18 h. The solvent was removed by evaporation in vacuo, whereafter the residue was partitioned between diethylether (50 ml)/water (50 ml). The organic phase was dried over $Na_2SO_4$, whereafter the title compound was precipitated from the solution with oxalic acid (0,25 g) dissolved in ethanol (5 ml). The crystals were collected by filtration and washed with ether, M.p. 181–°182° C.

In a similar manner the following compounds were prepared starting from the appropriate halides and 1-unsubstituted phenylpiperidines:
4-(3-cyclopropyl-1,2,4-oxadiazol-5-yl)-1-(2-ethoxyethyl)-4-phenylpiperidine oxalate, M.p. 188°–198° C. (Compound 17)
4-(3-cyclopropyl-1,2,4-oxadiazol-5-yl)-1-(2-methoxyethyl)-4-phenylpiperidine oxalate, M.p. 187°–188° C. (Compound 18)
1-cyclopropylmethyl-4-(3-cyclopropyl-1,2,4-oxadiazol-5-yl)-4-phenylpiperidine hydrochloride, M.p. 242°–243° C. (Compound 19)
1-(2-ethoxyethyl)-4-(3-methyl-1,2,4-oxadiazol-5-yl)-4-phenylpiperidine oxalate, M.p. 190°–193° C. (Compound 20)
1-(2-ethoxyethyl)-4-(3-phenyl-1,2,4-oxadiazol-5-yl)-4-phenylpiperidine oxalate, M.p. 170°–175° C. (Compound 21)
1-(2-phenoxyethyl)-4-(3-methyl-1,2,4-oxadiazol-5-yl)-4-phenylpiperidine oxalate, M.p. 184°–187° C. (Compound 22)
1-(2-(4-methoxyphenyl)ethyl)-4-(3-phenyl-1,2,4-oxadiazol-5-yl)-4-phenylpiperidine oxalate, M.p. 120°–150° C. (Compound 23)
1-(2-(diphenylmethoxy)ethyl)-4-(3-methyl-1,2,4-oxadiazol-5-yl)-4-phenylpiperidine oxalate, M.p. 201°–202° C. (Compound 24)

I claim:
1. A 4-phenylpiperidine compound having the formula I

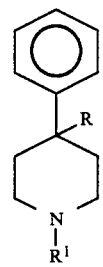

(I)

wherein
$R^1$ is hydrogen, ($C_{1-6}$-alkoxyaryl)alkyl, diphenylmethoxy-$C_{1-6}$-alkyl, $C_{1-8}$-alkyl, $C_d$ 4-10-cycloalkylalkyl, phenoxy- $C_{1-8}$-alkyl, or $C_{1-6}$-alkoxy-$C_{1-6}$-alkyl; and
R is

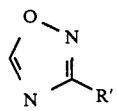

or $CH$=$NOR'$ wherein

R' is $C_{1-6}$-alkyl, $C_{3-7}$-cycloalkyl, $C_{1-6}$-alkoxy-$C_{1-6}$-alkyl, aryl-$C_{0-6}$-alkyl, which may optionally be substituted with one or more halogen and $C_{1-5}$-alkoxy, thienyl, or $C_{4-7}$-cycloalkylalkyl.

2. A compound of claim 1 which is 1-methyl-4-(3-phenyl-1,2,4-oxadiazol-5-yl)-4-phenylpiperidine.

3. A compound of claim 1 which is 4-(3-cyclopropyl-1,2,4-oxadiazol-5-yl)-4-phenylpiperidine.

4. A compound of claim 1 which is 4-methoxyiminomethyl-1-methyl-4-phenylpiperidine.

5. A compound of claim 1 which is 4-(3-cyclopropyl-1,2,4-oxadiazol-5-yl)-1-(2-ethoxyethyl)-4-phenylpiperidine.

6. A pharmaceutical composition suitable for use in the treatment of pain conditions comprising an amount of a compound of claim 1 which is effective for the alleviation of such pain conditions together with a pharmaceutically-acceptable carrier or diluent.

7. A pharmaceutical composition according to claim 6 wherein it is in the form of an oral dosage unit form containing 1–100 mg of the active compound.

8. A method of treating a pain condition in a subject in need of such treatment comprising the step of administering to said subject an amount of a compound of claim 1 which is effective for the alleviation of such pain condition.

* * * * *

UNITED STATES PATENT AND TRADEMARK OFFICE
CERTIFICATE OF CORRECTION

PATENT NO. : 4,845,095

DATED : July 4, 1989

INVENTOR(S) : Frank Watjen

It is certified that error appears in the above-identified patent and that said Letters Patent is hereby corrected as shown below:

Title Page, [56] References Cited, U.S. PATENT DOCUMENTS, line 1; "546/209" should read -- 346/209 --

Title Page, [57] Abstract, lines 3 and 4; "diphenylmethozy-" should read -- diphenylmethoxy- --

Col. 1, line 12; "assosiated" should read -- associated --

Col. 1, line 24; "analouges" should read -- analogues --

Col. 3, line 17; start a new paragraph with "(d)"

Col. 4, line 2; start a new paragraph with "The"

Col. 4, line 11; start a new paragraph with "Test"

Col. 5, line 43; "pharmaceuticallyacceptable" should read -- pharmaceutically acceptable --

Col. 6, line 51; "-5-yl) 4-" should read -- -5-yl)-4- --

Col. 6, line 57; "-5-yl) 4-" should read -- -5-yl)-4- --

Col. 7, line 59; "111,3°-111,6°C." should read -- 111.3-111.6°C. --

Col. 8, line 1; "99,9%" should read -- 99.9% --

UNITED STATES PATENT AND TRADEMARK OFFICE
CERTIFICATE OF CORRECTION

PATENT NO. : 4,845,095
DATED : July 4, 1989
INVENTOR(S) : Frank Watjen

It is certified that error appears in the above-identified patent and that said Letters Patent is hereby corrected as shown below:

Col. 8, line 57; "$C_d 4-10-$" should read -- $C_{4-10}-$ --

Signed and Sealed this

Twenty-ninth Day of May, 1990

*Attest:*

HARRY F. MANBECK, JR.

*Attesting Officer*   *Commissioner of Patents and Trademarks*